United States Patent
Qiu et al.

(10) Patent No.: US 10,458,953 B2
(45) Date of Patent: Oct. 29, 2019

(54) METHOD AND SYSTEM FOR ACQUIRING NATURAL FREQUENCY OF DIAPHRAGM

(71) Applicant: GOERTEK INC., WeiFang (CN)

(72) Inventors: Dong Qiu, WeiFang (CN); Chao Jiang, WeiFang (CN)

(73) Assignee: GOERTEK INC., Weifang (CN)

( * ) Notice: Subject to any disclaimer, the term of this patent is extended or adjusted under 35 U.S.C. 154(b) by 204 days.

(21) Appl. No.: 15/306,467

(22) PCT Filed: Apr. 1, 2015

(86) PCT No.: PCT/CN2015/075663
§ 371 (c)(1),
(2) Date: Oct. 24, 2016

(87) PCT Pub. No.: WO2015/161734
PCT Pub. Date: Oct. 29, 2015

(65) Prior Publication Data
US 2017/0045480 A1    Feb. 16, 2017

(30) Foreign Application Priority Data

Apr. 24, 2014   (CN) .......................... 2014 1 0167970

(51) Int. Cl.
*G01H 13/00*   (2006.01)
*G01N 29/12*   (2006.01)
(Continued)

(52) U.S. Cl.
CPC ............. *G01N 29/12* (2013.01); *G01H 3/00* (2013.01); *G01H 13/00* (2013.01); *H04R 7/12* (2013.01); *G01N 2291/014* (2013.01)

(58) Field of Classification Search
CPC ... G01N 29/12; G01N 2291/014; G01H 13/00
(Continued)

(56) References Cited

U.S. PATENT DOCUMENTS 4,872,335 A * 10/1989 Tsuruoka .............. G01L 9/0016
73/24.01

FOREIGN PATENT DOCUMENTS

CN     103219001 A     7/2013
CN     203165453 U     8/2013
(Continued)

OTHER PUBLICATIONS

Office Action from Korean Patent Office for Application No. 10-2016-7025945 dated May 18, 2017.
(Continued)

*Primary Examiner* — John E Chapman, Jr.

(57) ABSTRACT

A method and a system for acquiring the natural frequency of a diaphragm, wherein, the method comprises: selecting test frequency points in a closed space, converting an electric signal into an acoustic signal, directing sound into the closed space, and acquiring the acoustic pressure of each test frequency point; adjusting the electric signal until the acoustic pressure of each test frequency point is the same; converting the adjusted electric signal into an acoustic signal; acquiring the displacement generated by the vibration of the diaphragm; and taking the frequency corresponding to the maximum displacement of the diaphragm as the natural frequency of the diaphragm. By adopting the method and system, the natural frequency of the diaphragm is determined by acquiring the maximum displacement of the diaphragm. Moreover, the process of acquiring the natural frequency of the diaphragm is not affected by surrounding environment, and therefore the acquired result is more accurate.

10 Claims, 3 Drawing Sheets

(51) Int. Cl.
*H04R 7/12* (2006.01)
*G01H 3/00* (2006.01)

(58) Field of Classification Search
USPC .................................................. 73/597, 579
See application file for complete search history.

(56) References Cited

FOREIGN PATENT DOCUMENTS

| | | |
|---|---|---|
| CN | 103997706 A | 8/2014 |
| JP | 2002-090238 A | 3/2002 |
| TW | 200949261 A | 12/2009 |

OTHER PUBLICATIONS

Office Action from Chinese Patent Office for Application No. 201410167970.0, dated Oct. 26, 2016.
International Search Report for International Patent Application No. PCT/CN2015/075663 filed Apr. 1, 2015.

\* cited by examiner

METHOD AND SYSTEM FOR ACQUIRING NATURAL FREQUENCY OF DIAPHRAGM

CROSS-REFERENCE TO RELATED APPLICATIONS

The present specification is a U.S. National Stage of International Patent Application No. PCT/CN2015/075663 filed Apr. 1, 2015, which claims priority to and the benefit of Chinese Patent Application No. 201410167970.0 filed in the Chinese Intellectual Property Office on Apr. 24, 2014, the entire contents of which are incorporated herein by reference.

TECHNICAL FIELD

The present invention relates to technical field of diaphragm of a sounding device, and more particularly, to a method and system for acquiring the natural frequency of a diaphragm.

BACKGROUND ART

With rapid development of science and technology, the requirement on sounding devices is increasingly higher, and the performance of the diaphragm, which is a kernel component of the sounding device, directly influences the performance of the sounding device.

An important factor to evaluate the performance of the diaphragm is natural frequency. In prior art, a natural frequency of a diaphragm is acquired in such a way that the diaphragm is located in a unclosed environment, the diaphragm vibrates under the driving of an excitation sound source, and the frequency corresponding to the maximum sound pressure to which the diaphragm is subjected is taken as the natural frequency of the diaphragm.

Several problems exist in the above measurement method:

1) since the natural frequency of the diaphragm is acquired in a unclosed environment, the measurement result tends to be affected by surroundings, which results in a larger error in the measurement result;

2) when the frequency of the vibration of the diaphragm is equal to the natural frequency of the diaphragm, the amplitude of the vibration of the diaphragm is maximized, and because the amplitude of the vibration of the diaphragm may not be maximized when the diaphragm is subjected to the maximum sound pressure, it is not accurate to take the frequency corresponding to the maximum sound pressure to which the diaphragm is subjected as the natural frequency of the diaphragm;

3) the distortion amount generated when the diaphragm vibrates during acquisition of the natural frequency of the diaphragm cannot be acquired.

Consequently, there is a need for a novel technical solution capable of acquiring the natural frequency of the diaphragm.

SUMMARY

In view of the above problems, an objective of the present invention is to provide a method and a system for acquiring the natural frequency of a diaphragm to overcome the problem of technology biases existed in the existing method, the problem of easiness to be affected by surroundings during acquisition of the natural frequency of a diaphragm, and the problem of incapable of detecting the distortion amount generated when the diaphragm vibrates during acquisition of the natural frequency of the diaphragm.

A method for acquiring a natural frequency of a diaphragm provided by the present invention is used for acquiring the natural frequency of the diaphragm through a closed space formed by a structural cavity and the diaphragm. The method comprises a preprocessing stage for a sound pressure and an acquisition stage for the natural frequency of the diaphragm, wherein, the preprocessing stage for the sound pressure comprises:
selecting test frequencies in the closed space, converting an externally-input electric signal into an acoustic signal, emitting sound into the closed space, and acquiring a sound pressure received at each of the test frequencies respectively; and
adjusting the externally-input electric signal until a same sound pressure is received at each of the test frequencies in the closed space, and taking the electric signal at which the same sound pressure is acquired as an adjusted electric signal, wherein,
the acquisition stage for the natural frequency of the diaphragm comprises:
converting the adjusted electric signal into an acoustic signal and emitting sound into the closed space to vibrate the diaphragm;
acquiring displacements of the diaphragm when the diaphragm vibrates; and
taking a frequency corresponding to a maximum displacement among the acquired displacements as the natural frequency of the diaphragm.

A system for acquiring a natural frequency of a diaphragm provided by the present invention comprises:
an excitation sound source device for vibrating the diaphragm according to an externally-input electric signal, wherein,
the excitation sound source device comprises a structural cavity and a driving unit, the structural cavity and the diaphragm constitute a closed space; the driving unit is used for converting the externally-input electric signal into an acoustic signal so as to emit sound into the closed space to vibrate the diaphragm;
a test frequency selection device for selecting test frequencies in the closed space;
a sound pressure acquisition device for acquiring a sound pressure received at each of the test frequencies respectively;
an electric signal adjustment device for adjusting the externally-input electric signal until a same sound pressure is received at each of the test frequencies in the closed space;
a displacement acquisition device for acquiring displacements of the diaphragm when the diaphragm vibrates; and
a natural frequency acquisition device for taking a frequency corresponding to a maximum displacement among the acquired displacements as the natural frequency of the diaphragm.

By adopting the above method and system for acquiring the natural frequency of the diaphragm, the natural frequency of the diaphragm can be determined by acquiring the maximum displacement of the diaphragm when the diaphragm vibrates; the process of acquiring the natural frequency of the diaphragm is not affected by the surrounding environment, therefore, the acquired natural frequency of the diaphragm is more accurate; and the distortion amount generated when the diaphragm vibrates can be detected.

In order to achieve the above and related objectives, one or more aspects of the present invention comprise the features detailed below and indicated particularly in the claims. The following illustration and appended drawings illustrate some exemplary aspects of the present invention in detail. However, these aspects only indicate some implementations of various implementations of the present invention. In addition, the present invention is intended to contain these aspects and the equivalents thereof.

BRIEF DESCRIPTION OF THE DRAWINGS

By referring to the descriptions in connection with the accompanying drawings and the contents of the claims, and with a full understanding of the present invention, other purposes and results of the present invention will be more clearly and easily understand. In the drawings:

Same reference numerals in all of the accompanying drawings indicate similar or corresponding features or functions.

DETAILED DESCRIPTION OF EMBODIMENTS

Various specific details are set forth in the following description to comprehensively understand one or more embodiments for sake of illustration. However, it is obvious that these embodiments can be implemented without such specific details. In other examples, known structures and devices are illustrated by block diagrams to facilitate describing one or more embodiments.

Hereinafter, particular embodiments of the present invention are described in connection with the accompanying drawings.

With driving force applied on a diaphragm, the diaphragm will resonate when the vibration frequency of the diaphragm is the same as the natural frequency of the diaphragm, and at this time the amplitude of the vibration of the diaphragm (the amplitude of the vibration of the diaphragm is indicated by the displacement, the amplitude is in direct proportion to the displacement, i.e., the larger the amplitude, the larger the displacement) is maximized. However, in the above conventional method for acquiring the natural frequency of a diaphragm, by acquiring the maximal sound pressure received by the diaphragm, the frequency corresponding to the maximal sound pressure is taken as the natural frequency of the diaphragm, which is not accurate enough. Furthermore, during the acquisition of the natural frequency of the diaphragm, the distortion amount generated when the diaphragm vibrates may not be acquired, and meanwhile, the natural frequency of the diaphragm is acquired in an unclosed environment, the result tends to be affected by surroundings.

In the present invention, the diaphragm is arranged in a closed space, the natural frequency of the diaphragm is determined by acquiring the maximum value of the amplitude of the vibration of the diaphragm, and a device for detecting the distortion of the diaphragm is provided during the acquisition, thereby detecting the distortion amount generated when the diaphragm vibrates.

It should be noted that, the diaphragm is arranged in a closed space which is a closed space constituted by the diaphragm and the structural cavity, i.e., one side of the diaphragm is located inside the closed space, and the other side of the diaphragm is located outside the closed space.

Figure 1:
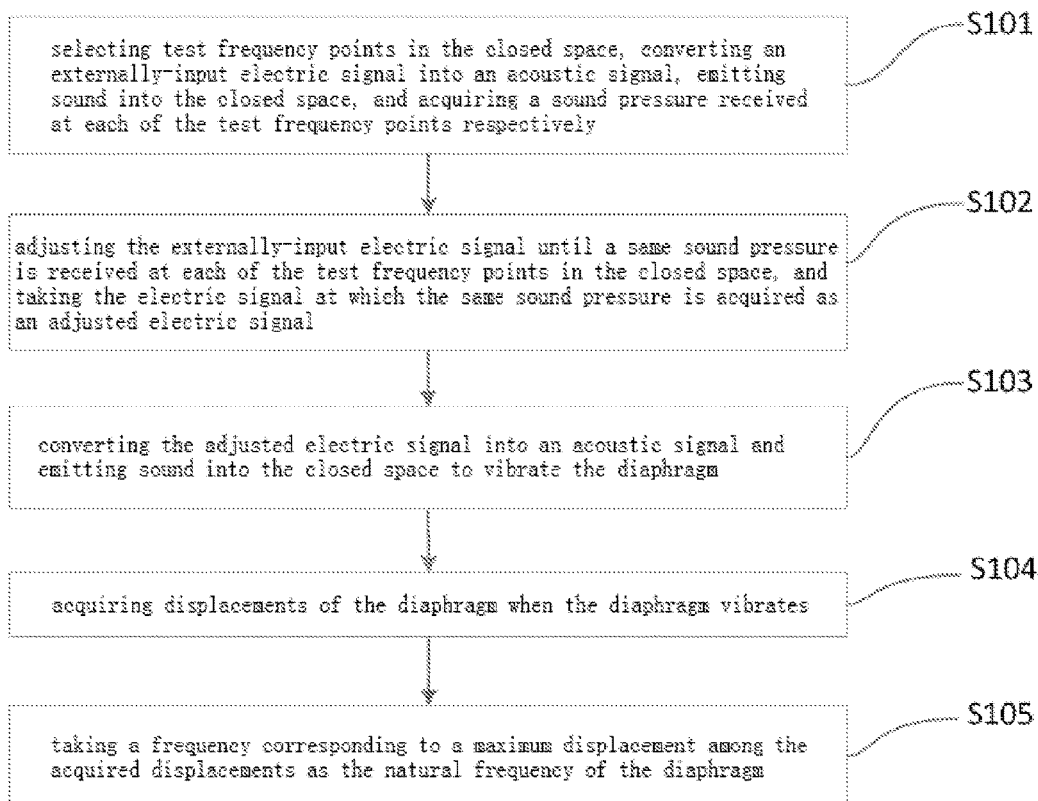
FIG. 1 is a flowchart illustrating a method for acquiring the natural frequency of the diaphragm according to the embodiments of the present invention.

FIG. 1 illustrates the processes of the method for acquiring the natural frequency of the diaphragm according to the embodiments of the present invention.

As shown in FIG. 1, the method for acquiring the natural frequency of a diaphragm provided by the present invention comprises two stages:

Preprocessing Stage

Step S101: selecting test frequencies in the closed space, converting an externally-input electric signal into an acoustic signal, emitting sound into the closed space, and acquiring the sound pressure received at each of the test frequencies respectively.

It should be noted that, the selected test frequencies may be all test frequencies in the closed space, but a part of the test frequencies in the closed space may be selected as the test frequencies, so as to determine a frequency range for acquisition, and then by traversing each of the selected test frequencies, the sound pressure received at each of the test frequencies is acquired.

Step S102: adjusting the externally-input electric signal so that the sound pressure received at each of the test frequencies in the closed space is the same.

It should be noted that, the externally-input electric signal is adjusted by adjusting the voltage values of sine electric signals with different frequencies in the frequency range for acquisition, and the adjusted electric signal should be a continuously variable electric signal.

Acquisition Stage

Step S103: converting the adjusted electric signal into an acoustic signal, and emitting sound into the closed space to vibrate the diaphragm.

Wherein, the adjusted electric signal is the externally-input electric signal. If the externally-input electric signal is strong enough, the acoustic signal converted from the externally-input electric signal is capable of vibrating the diaphragm, and at this time, the externally-input electric signal is not required to be amplified. If the intensity of the externally-input electric signal is weak, the acoustic signal converted from the externally-input electric signal is insufficient to vibrate the diaphragm, and at this time, the externally-input electric signal is required to be amplified, and then the amplified electric signal is converted into an acoustic signal to vibrate the diaphragm.

In most cases, the externally-input electric signal is an electric signal output by a data acquisition card. As the electric signal output by the data acquisition card has a rated intensity, the electric signal output by the data acquisition card is required to be amplified, and particularly, the electric signal output by the data acquisition card is amplified by a power amplifier.

Step S104: acquiring the displacements of the diaphragm when the diaphragm vibrates.

During acquisition of the displacements of the diaphragm when the diaphragm vibrates, firstly, a vibration displacement signal corresponding to a displacement is acquired, and then the vibration displacement signal is converted into an electric signal so as to acquire the converted electric signal, and thus the acquired and converted electric signal is the displacement of the diaphragm when the diaphragm vibrates.

Particularly, the vibration displacement signal is acquired by a laser position finder, and then the vibration displacement signal is converted into an electric signal by a demodulator corresponding to the laser position finder, and then the converted electric signal is acquired by a data acquisition card to be taken as the displacement of the diaphragm when the diaphragm vibrates.

The vibration displacement signal is acquired by a laser position finder, and the specific procedure is that: the laser head of the laser position finder emits a laser beam towards the vibrating diaphragm, and the reflected vibration displacement signal is displayed on the CCD (imaging sensor) of the laser position finder as one point with reference to the center point of the CCD, and the displacement from the point displayed on the CCD to the center point is the displacement of the diaphragm when the diaphragm vibrates, and the vibration displacement signal is converted into an electric signal by a demodulator corresponding to the laser position finder.

In the present invention, a Doppler vibration meter may be used for acquiring the displacement of the diaphragm when the diaphragm vibrates, the specific procedure is that: the laser head of the Doppler vibration meter emits a laser beam with a certain frequency towards the vibrating diaphragm, and the reflected light onto the Doppler vibration meter has a certain frequency as well; and by using the variation (frequency shift caused by vibration of the diaphragm) on frequency of the reflected light received by the CCD on the Doppler vibration meter with respect to the emitted light, the variation on velocity of vibration of the diaphragm is acquired, and the variation on velocity is acquired by a demodulator corresponding to the Doppler vibration meter; and the variation on velocity in a preset time period is integrated so as to acquire the displacement of the diaphragm when the diaphragm vibrates, and the displacement is then converted into an electric signal corresponding to the displacement.

It should be noted that, the Doppler vibration meter is suitable for acquiring the displacement of a diaphragm with a higher vibration frequency, and larger error will be generated when the Doppler vibration meter is used for acquiring the displacement of a diaphragm with a lower vibration frequency. However, the laser position finder may acquire both the displacement of a diaphragm with a higher vibration frequency, and the displacement of a diaphragm with a lower vibration frequency, and a proper device may be chosen based on practical requirements.

While acquiring the displacements of the diaphragm when the diaphragm vibrates, the distortion amount generated when the diaphragm vibrates is acquired. During acquisition of the distortion amount generated when the diaphragm vibrates, the sound pressure radiated due to vibration of the diaphragm and the sound pressure radiated by the surroundings are respectively acquired by a sound pressure sensor which is provided at a position outside the closed space and close to the diaphragm, the sound pressure radiated due to vibration of the diaphragm and the sound pressure radiated by the surroundings are converted into electric signals respectively, and the distortion amount generated when the diaphragm vibrates is acquired by using the converted electric signals.

Wherein, the sound pressure radiated due to vibration of the diaphragm is useful, and is referred to as a useful signal; the sound pressure generated by the surroundings is useless, and is referred to as a useless signal. The useful and useless signals are combined after they are converted into electric signals, and a useless signal separated from the combined electric signals by a software is the distortion amount when the diaphragm vibrates.

As the excitation sound source device generates sound to apply an upward sound pressure on the diaphragm, and the noise generated by the surroundings will apply a downward sound pressure on the diaphragm, the displacement of the diaphragm will be affected by the sound pressure of the noise, and the test frequency corresponding to such displacement is a problem point. After completion of the entire acquisition, all the problem points in the test test frequencies are removed so as to avoid influence by the noise generated by the surroundings.

Step S105: taking the frequency corresponding to the maximum displacement generated by the vibration of the diaphragm as the natural frequency of the diaphragm.

It should be noted that, the structural cavity is originally enclosed, but in order to arrange the diaphragm in a closed space, an opening should be provided in the structural cavity, and the diaphragm is fitted to the opening to be fixed, and thus the coverage area of the sound pressure on the diaphragm is the area of the opening.

As the sound pressure received at each of the test frequencies in the closed space is the same and the coverage areas of the sound pressures on the diaphragm are the same, the driving force applied on each of the test frequencies is the same. In the case of constant quality of the diaphragm, the maximal displacement of vibration of the diaphragm (i.e., the maximal amplitude of the diaphragm) may be acquired at the natural frequency of the diaphragm, and the frequency corresponding to the maximum displacement is the natural frequency of the diaphragm.

The above procedures describe the method for acquiring the natural frequency of a diaphragm according to the embodiments of the present invention, the method may be used for acquiring the natural frequency of the diaphragm in a closed space without influence by the surroundings and the quality of the diaphragm, so that the acquisition of the natural frequency of the diaphragm is more direct, and more credible.

Figure 2:
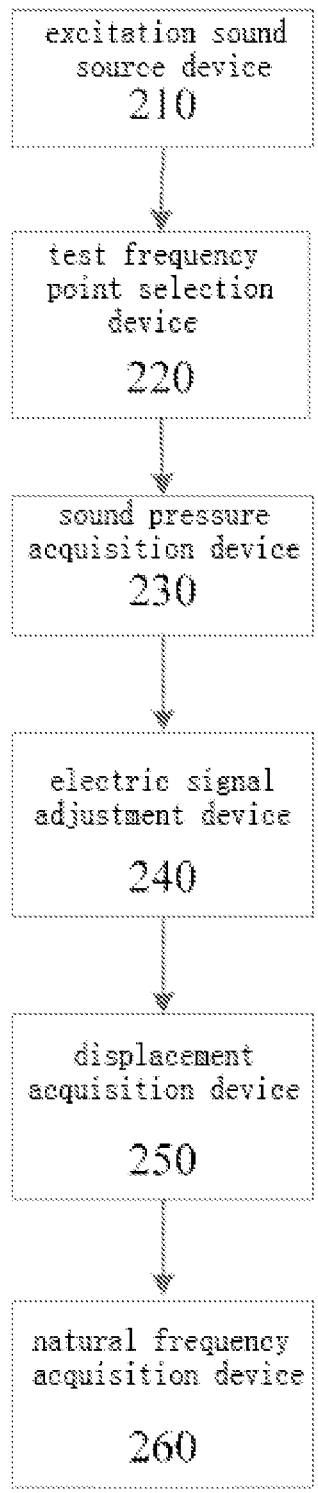
FIG. 2 is a logic structure diagram illustrating a system for acquiring the natural frequency of the diaphragm according to the embodiments of the present invention.

A system for acquiring the natural frequency of a diaphragm, which system corresponds to the above method, is further provided by the present invention. FIG. 2 is illustrates the logical structure of the system for acquiring the natural frequency of a diaphragm according to the embodiments of the present invention.

As illustrated in FIG. 2, the system for acquiring the natural frequency of a diaphragm according to the present invention comprises an excitation sound source device 210, a test frequency selection device 220, a sound pressure acquisition device 230, an electric signal adjustment device 240, a displacement acquisition device 250 and a natural frequency acquisition device 260.

Wherein, the excitation sound source device 210 is used for vibrating the diaphragm 231 according to the externally-input electric signal; the excitation sound source device 210 comprises a structural cavity 211 and a driving unit 212, and the structural cavity 211 and the diaphragm 231 constitute a closed space; the driving unit 212 is used for converting the externally-input electric signal into an acoustic signal and emitting sound into the closed space to vibrate the diaphragm 231; the test frequency selection device 220 is used for selecting the test frequencies in the closed space; the sound pressure acquisition device 230 is used for acquiring the sound pressure received at each of the test frequencies respectively; the electric signal adjustment device 240 is used for adjusting the externally-input electric signal so that the sound pressure received at each of the test frequencies in the closed space is the same; the displacement acquisition device 250 is used for acquiring the displacements of the diaphragm when the diaphragm vibrates; the natural frequency acquisition device 260 is used for taking the frequency corresponding to the maximum displacement among the acquired displacements as the natural frequency of the diaphragm.

Wherein, the system for acquiring the natural frequency of a diaphragm further comprises a signal amplifying device (not illustrated) for amplifying the externally-input electric signal, and the driving unit 212 converts the amplified electric signal into an acoustic signal to vibrate the diaphragm 231.

Wherein, an opening is provided on the structural cavity 211, and the diaphragm 231 is fitted and fixed on the opening so that the structural cavity 211 with the diaphragm 231 form a closed space, and thus the area of the opening is the coverage area of the sound pressure on the diaphragm 231.

Wherein, the displacement acquisition device 250 comprises a vibration displacement signal acquisition unit (not illustrated), a demodulation unit (not illustrated) and a signal acquisition unit (not illustrated), wherein the vibration displacement signal acquisition unit is used for acquiring the vibration displacement signal corresponding to the displacement, the demodulation unit is used for converting the vibration displacement signal into an electric signal, and the signal acquisition unit is used for acquiring the converted electric signal as the displacement of the diaphragm when the diaphragm vibrates.

It should be noted that, the displacement acquisition device 250 may employ the laser position finder or Doppler vibration meter in the above method, and may employ other device capable of acquiring the displacement of the diaphragm when the diaphragm vibrates as well. The demodulation unit may be a demodulator corresponding to the laser position finder in the above method or a demodulator corresponding to the Doppler vibration meter, and may be a demodulation device corresponding to other device as well. The signal acquisition unit may be a CCD (imaging sensor) in the above method, and may be other device for acquiring electric signal as well. The sound pressure acquisition device 230 and the sound pressure sensor may be a sound pressure field microphone, or other device for acquiring sound pressure.

The system for acquiring the natural frequency of a diaphragm further comprises a distortion amount acquisition device 270 for acquiring the distortion amount generated when the diaphragm vibrates, wherein, the distortion amount acquisition device 270 is a sound pressure sensor which is preset at a position outside the closed space and close to the diaphragm, and used for acquiring the sound pressure radiated due to vibration of the diaphragm and the sound pressure radiated by the surroundings, the sound pressure radiated due to vibration of the diaphragm and the sound pressure radiated by the surroundings are converted into electric signals by the driving unit 212 respectively, and the distortion amount generated when the diaphragm vibrates is acquired by using the converted electric signals. In a preferred embodiment, a sound pressure field microphone is selected as a sound pressure sensor.

Figure 3:
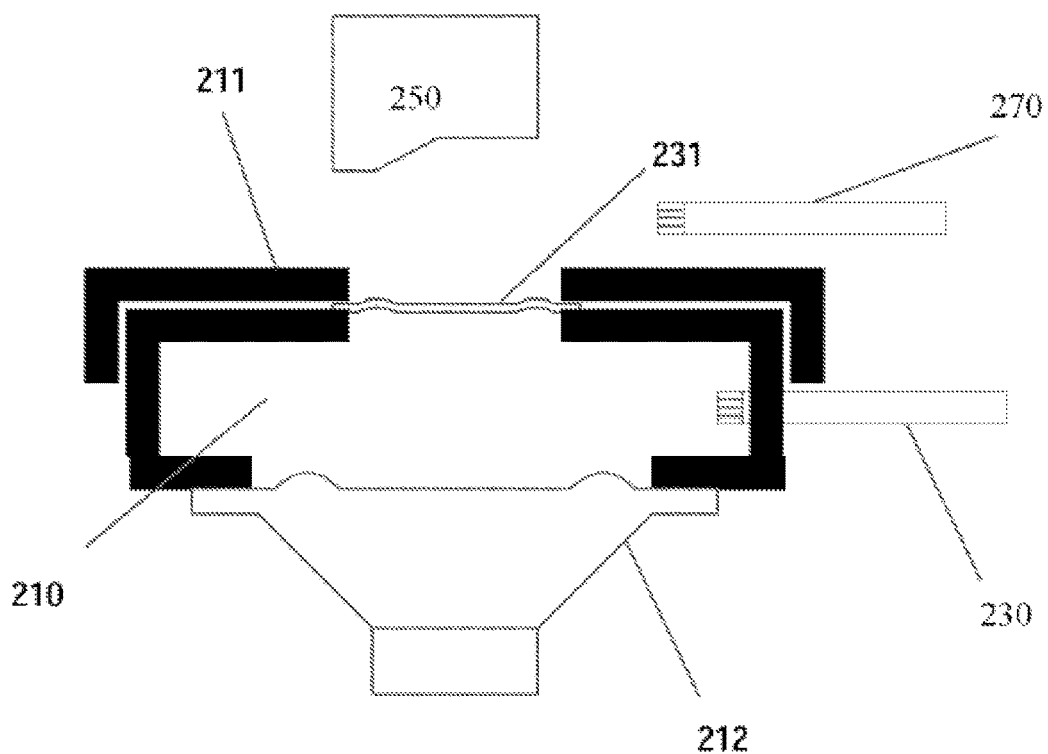
FIG. 3 is an entire structure diagram illustrating a system for acquiring the natural frequency of the diaphragm according to the embodiments of the present invention.

In order to illustrate the system for acquiring the natural frequency of a diaphragm according to the present invention more visually, FIG. 3 illustrates the entire structure of the system for acquiring the natural frequency of a diaphragm and the circuit of the system for acquiring the natural frequency of a diaphragm according to the embodiments of the present invention. As illustrated in FIG. 3, the excitation sound source device 210 of the present invention comprises a structural cavity 211 and a driving unit 212, and the structural cavity 211 and the diaphragm 231 constitute a closed space. The driving unit 212 and the diaphragm 231 are provided at two opposite surfaces of the structural cavity 211, and this arrangement enables the driving unit 212 to vibrate the diaphragm. The displacement acquisition device 250 is provided in front of the diaphragm 231 to acquire the displacement of the diaphragm when the diaphragm 231 vibrates. The distortion amount acquisition device 270 is provided at the position outside the closed space and close to the diaphragm 231 to acquire the sound pressure radiated due to vibration of the diaphragm 231 and the sound pressure radiated by the surroundings. The sound pressure acquisition device 230 is provided in the lateral surface of the structural cavity 211 to acquire the sound pressure radiated due to vibration of the diaphragm 231.

As described above, the method and system for acquiring the natural frequency of a diaphragm provided by the present invention is described by way of example with reference to the accompanying drawings. However, it should be understood by those skilled in the art that various improvements on details achieved therein can be made to the method and system for acquiring the natural frequency of a diaphragm provided by the present invention as described above without depart from the contents of the present invention. Accordingly, the scope of protection of the present invention is determined by the contents of the appended claims.

The invention claimed is:

1. A method for acquiring a natural frequency of a diaphragm, wherein, the natural frequency of the diaphragm is acquired through a closed space formed by a structural cavity and the diaphragm, and the method comprising a preprocessing stage for a sound pressure and an acquisition stage for the natural frequency of the diaphragm, wherein, the preprocessing stage for the sound pressure comprises:

selecting test frequencies, converting an externally-input electric signal into an acoustic signal, emitting sound into the closed space, and acquiring a sound pressure received at each respective test frequency; and adjusting the externally-input electric signal until a same sound pressure is received at each test frequency, and taking the electric signal at which the same sound pressure is acquired as an adjusted electric signal, and wherein, the acquisition stage for the natural frequency of the diaphragm comprises:

converting the adjusted electric signal into an acoustic signal and emitting sound into the closed space to vibrate the diaphragm in response to the adjusted electrical signal;

acquiring displacements of the diaphragm when the diaphragm vibrates; and taking a frequency corresponding to a maximum displacement among the acquired displacements as the natural frequency of the diaphragm.

2. The method of claim 1, wherein, during acquisition of the displacements of the diaphragm when the diaphragm vibrates, a vibration displacement signal corresponding to a displacement is acquired, and then the vibration displacement signal is converted into an electric signal, and the converted electric signal is acquired as the displacement of the diaphragm when the diaphragm vibrates.

3. The method of claim 1, wherein, during a process of vibrating the diaphragm according to the externally-input electric signal, the externally-input electric signal is amplified, and the amplified electric signal is converted into an acoustic signal to vibrate the diaphragm.

4. The method of claim 1, wherein,
an opening is provided on the structural cavity, and the diaphragm is fitted and fixed on the opening so that the structural cavity with the diaphragm form the closed space;
an area of the opening is a coverage area of the sound pressure on the diaphragm.

5. The method of claim 1, wherein, while acquiring the displacements of the diaphragm when the diaphragm vibrates, a distortion amount generated when the diaphragm vibrates is acquired, wherein, during acquisition of the distortion amount generated when the diaphragm vibrates,
a sound pressure radiated due to vibration of the diaphragm and a sound pressure radiated by surroundings are respectively acquired by a sound pressure sensor which is preset at a position outside the closed space and close to the diaphragm,
the sound pressure radiated due to vibration of the diaphragm and the sound pressure radiated by surroundings are converted into electric signals respectively, and
the distortion amount generated when the diaphragm vibrates is acquired by using the converted electric signals.

6. A system for acquiring a natural frequency of a diaphragm, comprising:
an excitation sound source device for vibrating the diaphragm according to an externally-input electric signal, wherein, the excitation sound source device comprises a structural cavity and a driving unit, the structural cavity and the diaphragm constitute a closed space, and the driving unit is used for converting the externally-input electric signal into an acoustic signal so as to emit sound into the closed space to vibrate the diaphragm;
a test frequency selection device for selecting test frequencies;
a sound pressure acquisition device for acquiring a sound pressure received at each of the test frequencies, respectively;
an electric signal adjustment device for adjusting the externally-input electric signal until a same sound pressure is received at each of the test frequencies in the closed space;
a displacement acquisition device for acquiring displacements of the diaphragm when the diaphragm vibrates in response to the adjusted signal; and
a natural frequency acquisition device for taking a frequency corresponding to a maximum displacement among the acquired displacements as the natural frequency of the diaphragm.

7. The system of claim 6, further comprising a signal amplifying device for amplifying the externally-input electric signal, wherein,
the driving unit converts the amplified electric signal into an acoustic signal to vibrate the diaphragm.

8. The system of claim 6, wherein,
an opening is provided on the structural cavity, and the diaphragm is fitted and fixed on the opening so that the structural cavity with the diaphragm form the closed space;
an area of the opening is a coverage area of the sound pressure on the diaphragm.

9. The system of claim 6, wherein,
the displacement acquisition device comprises:
a vibration displacement signal acquisition unit for acquiring a vibration displacement signal corresponding to a displacement;
a demodulation unit for converting the vibration displacement signal into an electric signal; and
a signal acquisition unit for acquiring the converted electric signal as the displacement of the diaphragm when the diaphragm vibrates.

10. The system of claim 6, further comprising a distortion amount acquisition device for acquiring a distortion amount generated when the diaphragm vibrates, wherein,
the distortion amount acquisition device comprises a sound pressure sensor which is preset at a position outside the closed space and close to the diaphragm,
the sound pressure sensor is used for respectively acquiring a sound pressure radiated due to vibration of the diaphragm and a sound pressure radiated by surroundings,
the sound pressure radiated due to vibration of the diaphragm and the sound pressure radiated by surroundings are converted into electric signals by the driving unit respectively, and
the distortion amount generated when the diaphragm vibrates is acquired by using the converted electric signals.

* * * * *